United States Patent
Salo

(10) Patent No.: US 10,866,078 B2
(45) Date of Patent: Dec. 15, 2020

(54) ARRANGEMENT AND A METHOD FOR INSERTING AND REMOVING A HEAD OF A MEASURING DEVICE TO AND FROM A PROCESS SPACE

(71) Applicant: VAISALA OYJ, Helsinki (FI)

(72) Inventor: Harri Salo, Vantaa (FI)

(73) Assignee: VAISALA OYJ, Helsinki (FI)

( * ) Notice: Subject to any disclaimer, the term of this patent is extended or adjusted under 35 U.S.C. 154(b) by 138 days.

(21) Appl. No.: 16/003,955

(22) Filed: Jun. 8, 2018

(65) Prior Publication Data

US 2018/0356315 A1 Dec. 13, 2018

(30) Foreign Application Priority Data

Jun. 12, 2017 (FI) ..................................... 20175540
May 18, 2018 (FI) ..................................... 20185464

(51) Int. Cl.
  *G01B 5/00* (2006.01)
  *G01F 15/00* (2006.01)
  (Continued)

(52) U.S. Cl.
  CPC ........... *G01B 5/0002* (2013.01); *F01D 17/02* (2013.01); *F01D 21/003* (2013.01);
  (Continued)

(58) Field of Classification Search
  CPC ....... G01F 15/00; G01F 15/18; G01N 27/283; G01N 1/2035; G01N 2001/205; G01N 33/00; G01N 2021/9542; G01B 5/0004; G01B 5/0002; Y10T 137/612; Y10T 137/0458; Y10T 29/53848; G01D 11/00; F01D 21/003; F01D 25/285; F01D 17/02;
  (Continued)

(56) References Cited

U.S. PATENT DOCUMENTS 3,152,479 A    10/1964   Small
3,648,970 A *   3/1972   Hartmann ............... F16K 35/06
                                                                       251/104
(Continued)

FOREIGN PATENT DOCUMENTS

FI                118442 B     11/2007

OTHER PUBLICATIONS

Finnish Search Report of Finnish Patent Application No. 20175540, dated Jan. 18, 2018.

*Primary Examiner* — Eric S. McCall
*Assistant Examiner* — Timothy P Graves
(74) *Attorney, Agent, or Firm* — Buchanan Ingersoll & Rooney PC

(57) ABSTRACT

An arrangement and method are disclosed for inserting and removing a head of a measuring device to and from a process space. The arrangement includes a measuring device with a measuring head and a retractor tool connected to a valve member. The retractor tool includes rails, a cradle for receiving the measuring device and arranged to slide along the rails, and a driving mechanism for moving the cradle. A valve lock mechanism prevents opening of the valve member if the measuring device is not at a location barring a fluid flow from the process space, and the head of the measuring device is insertable to the process space when the measuring device is received in the cradle.

18 Claims, 15 Drawing Sheets

(51) Int. Cl.
- *G01F 15/18* (2006.01)
- *G01D 11/00* (2006.01)
- *F01D 17/02* (2006.01)
- *F01D 25/28* (2006.01)
- *F16M 11/04* (2006.01)
- *F16M 11/20* (2006.01)
- *F16M 11/42* (2006.01)
- *G01N 33/00* (2006.01)
- *G01N 27/28* (2006.01)
- *F01D 21/00* (2006.01)
- *G01N 1/20* (2006.01)
- *G01N 21/954* (2006.01)

(52) U.S. Cl.
CPC ........... *F01D 25/285* (2013.01); *F16M 11/04* (2013.01); *F16M 11/20* (2013.01); *F16M 11/425* (2013.01); *G01B 5/0004* (2013.01); *G01D 11/00* (2013.01); *G01F 15/00* (2013.01); *G01F 15/18* (2013.01); *G01N 1/2035* (2013.01); *G01N 27/283* (2013.01); *G01N 33/00* (2013.01); *F05D 2260/80* (2013.01); *F05D 2260/83* (2013.01); *G01N 2001/205* (2013.01); *G01N 2021/9542* (2013.01); *Y10S 901/44* (2013.01); *Y10T 29/53848* (2015.01); *Y10T 137/0458* (2015.04); *Y10T 137/612* (2015.04)

(58) Field of Classification Search
CPC ............. F05D 2260/80; F05D 2260/83; Y10S 901/44; F16M 11/425; F16M 11/04; F16M 11/20
See application file for complete search history.

(56) References Cited

U.S. PATENT DOCUMENTS

| | | |
|---|---|---|
| 4,218,918 A | 8/1980 | Ueno et al. |
| 4,817,293 A | 4/1989 | Daverio et al. |
| 4,823,623 A | 4/1989 | Carpenter et al. |
| 2007/0051194 A1 | 3/2007 | Salo |
| 2009/0262354 A1* | 10/2009 | Horiuchi ................ G01N 21/55 356/445 |
| 2012/0125131 A1 | 5/2012 | Sue et al. |
| 2015/0090054 A1 | 4/2015 | Leidner |
| 2016/0011080 A1* | 1/2016 | Moore .................. F01D 25/285 73/112.01 |

* cited by examiner

ARRANGEMENT AND A METHOD FOR INSERTING AND REMOVING A HEAD OF A MEASURING DEVICE TO AND FROM A PROCESS SPACE

FIELD OF THE INVENTION

The present invention relates to an arrangement and a method for inserting and removing a head of a measuring device to and from a process space, and particularly to an arrangement and a method for inserting and removing a head of a measuring device to and from a process space comprising a retractor tool.

BACKGROUND OF THE INVENTION

Measuring devices are used in monitoring and managing processes where the process medium may be hot, pressurized, aggressive or otherwise hazardous. If the process is a continuous process with infrequent shutdowns there is a need for servicing and maintenance of the measuring devices while the process line is under full process flow and pressure. The servicing and maintenance may comprise modifying, maintaining, lubricating, cleaning and un-jamming the measuring devices.

There is a need for failsafe and fool proof solutions for servicing and maintenance activities of measuring devices in order to prevent injuries resulting from failure to use practices and procedures necessary. Further, the tools used in handling a measuring device while the process line is under full process flow and pressure should be designed to protect the user.

BRIEF DESCRIPTION OF THE INVENTION

An object of the present invention is to provide an arrangement and a method to solve the above problems. The objects of the invention are achieved by an arrangement and a method for inserting and removing a head of a measuring device to and from a process space which are characterized by what is stated in the independent claims. The preferred embodiments of the invention are disclosed in the dependent claims.

The invention is based on the idea of providing an arrangement for inserting and removing a head of a measuring device to and from a process space. The arrangement comprising a process space, a measuring device comprising a measuring head at its one end and a retractor tool, wherein a valve member is connected to the process space and the retractor tool is connected to the valve member. The retractor tool comprises rails, the first ends of the rails are attached to the valve member and the second ends of the rails are connected with a cross beam, a cradle for receiving the measuring device and arranged to slide along the rails, the measuring device is arranged to slide between the rails when received in the cradle, and a driving mechanism for moving the cradle, and the arrangement comprises an valve lock mechanism preventing opening of the valve member when the measuring device is not at a location barring a fluid flow from the process space, and the head of the measuring device is insertable to the process space and removable from the process space when the measuring device is received in the cradle.

The invention is based on the idea of providing a method for inserting and removing a head of a measuring device to and from a process space. The method comprising a process space, a measuring device comprising a measuring head at its one end and a retractor tool, wherein a valve member is connected to the process space and the retractor tool is connected to the valve member. The retractor tool comprises rails, the first ends of the rails are attached to the valve member and the second ends of the rails are connected with a cross beam, a cradle and a driving mechanism, wherein the cradle receives the measuring device and slides along the rails, in the method the measuring device slides between the rails when received in the cradle, and the driving mechanism moves the cradle. The method comprises a valve lock mechanism preventing opening of the valve member when the measuring device is not at a location barring a fluid flow from the process space, and the head of the measuring device is inserted to the process space and removed from the process space by putting the measuring device in the cradle and operating the driving mechanism and the valve member.

The arrangement and method provide a failsafe operation and a fool proof construction. The arrangement and the method protect user from spills and splashes during the measuring device insertion and removal.

BRIEF DESCRIPTION OF THE FIGURES

In the following the invention will be described in greater detail by means of preferred embodiments with reference to the attached drawings, in which.

DETAILED DESCRIPTION OF THE INVENTION

Figure 1:
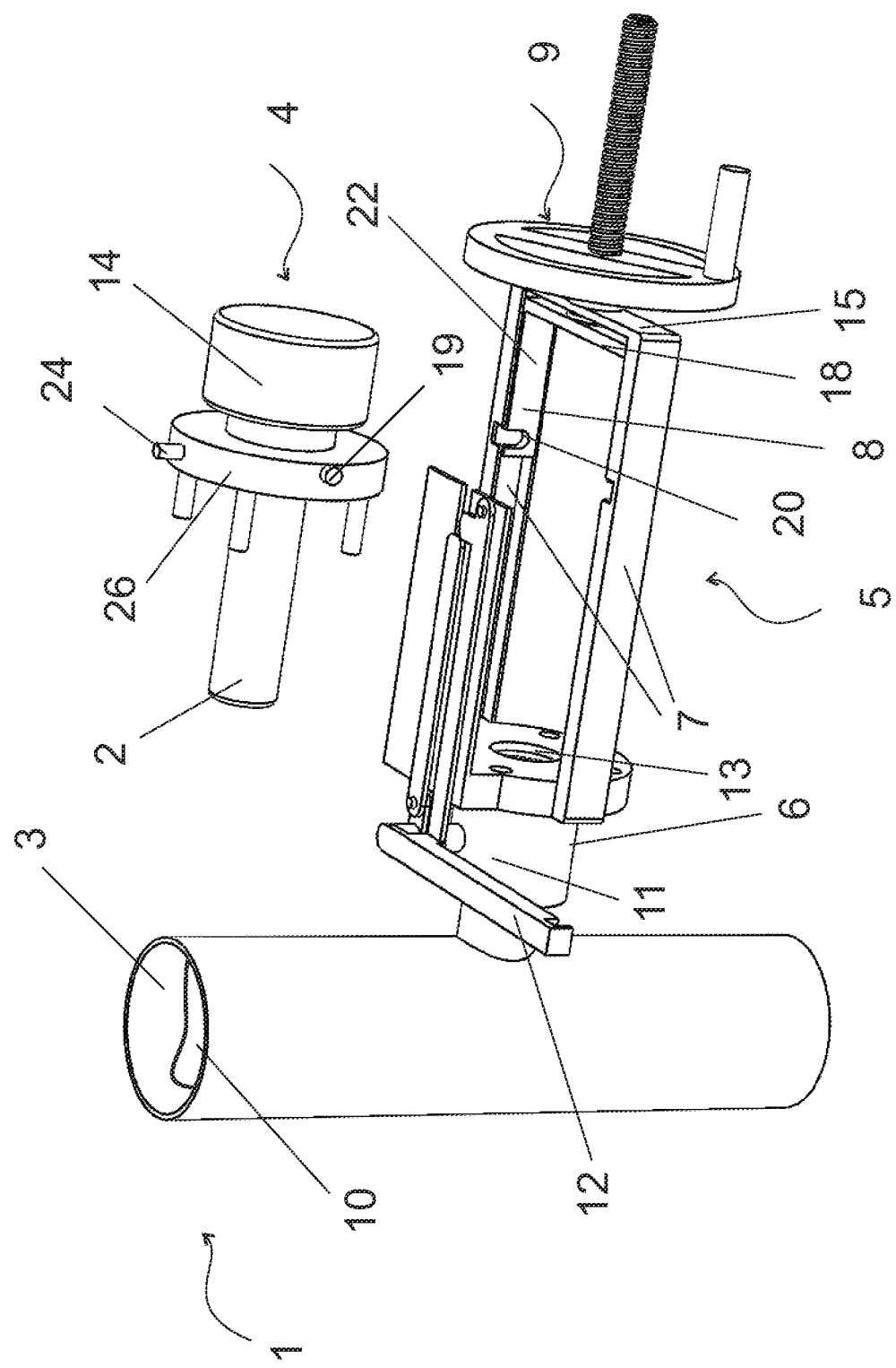
FIG. 1 shows an arrangement where a measuring device is uninstalled to a retractor tool.

FIG. 1 shows an embodiment of an arrangement 1 for inserting and removing a head of a measuring device 2 to and from a process space 3. The arrangement 1 comprises a process space 3, a measuring device 4 comprising a measuring head 2 at its one end and a retractor tool 5. In FIG. 1 the measuring device 4 is shown uninstalled to the retractor tool 5 for a sake of clarity. A valve member 6 is connected to the process space 3 and the retractor tool 5 is connected to the valve member 6. The retractor tool 5 comprises rails 7, a cradle 8 for receiving the measuring device 4 and arranged to slide along the rails 7, and a driving mechanism 9 for moving the cradle 8. The arrangement comprises a valve lock mechanism preventing opening of the valve member 6 if the measuring device 4 is not present in the cradle 8, and the head of the measuring device 2 is insertable to the process space 3 and removable from the process space 3 by putting the measuring device 4 in the cradle 8 and operating the driving mechanism 9 and the valve member 6.

The process space 3 may be a process pipe, for instance. In the Figures illustrated process space 3 is a part of a process pipe. The process space 3 contains the fluid 10 to be measured with the measuring device 4. The fluid 10 may be pressurized, hot and/or aggressive. An example of the process space 3 and the fluid 10 is a line comprising black liquor.

The valve member 6 closes the opening to the process space 3. The valve member 6 comprising an isolation valve 11, may be attached to the process space 3 in any manner known per se, for example by means of a welded stub pipe and a flange joint. The isolation valve 11 itself may be any type of valve suitable for the process pressure and process fluid, such as a ball valve, a suitable slide valve, etc. The isolation valve 11 isolates process fluid 10 from the surroundings. The valve member 6 comprises a valve handle 12 operating the isolation valve 11, i.e. the valve member 6 is closed or opened by rotating the valve handle 12. The valve member comprises a sealing gasket part 13 for sealing the gap between the measurement device 4 and the valve body.

The opening and closing of the valve member 6 while the process line is under full process flow and pressure may present a hazard to the user. Therefore the arrangement 1 comprises a valve lock mechanism preventing opening of the valve member 6 if the measuring device 4 is not present in the cradle 8.

A measuring device 4 may be a sensor, an analyser or an optical analyser, for instance. The measuring device 4 is used for monitoring a process and/or to manage a process, for instance. The head of measuring device 2 is inserted to the process space 3 to be in contact with the fluid 10 to be measured and the body of the measuring device 14 extends outside the process space 3. The body 14 comprises typically a housing comprising an electronics, a processing unit, or an output unit or any combination of these.

An optical analyser or an optical sensor may be a refractometer. Refractometers are commonly used to determine the concentration of a dissolved solids by making an optical measurement of a solution's Refractive Index. The head of an optical analyser or sensor typically comprise an optical window, e.g. a prism, and a temperature sensor which are inserted to the process space to be in contact with the fluid to be measured. The body of an optical analyser or sensor typically comprises one or more of the following: a light source, a camera, an analysis circuit, a processor card.

The retractor tool 5 is an equipment for inserting and removing the measuring device 4 to and from the process space 3. The head of the measuring device 2 is inserted or removed from the process space 3 and the body of the measuring device 14 extends outside the process space 3 also when the head 2 is in an inserted position. The measuring device 4 is guided and supported by the retractor tool 5.

The retractor tool 5 is fixed to the valve member 6. If the retractor tool 5 is permanently fixed to the valve member 6 the falling of the retractor tool 5 and the measurement device 4 is fully prevented. The retractor tool 5 allows a synchronized movements between the valve member 6 and the measuring device 4 during the inserting and removing the head of the measuring device 2 to and from the process space 3.

The retractor tool 5 comprises a rail part. In the rail part the rails 7 form the long sides of the retractor tool 5 and the rails 7 are connected with a cross beam 15. The retractor tool 5 may also comprise more than two rails 7, a third rail may be provided below and between the two rails 7, for instance. In Figures the retractor tool 5 is fixed to the valve member 6 by attaching the ends 34 of the rails 7 to the flange of the isolation valve 25. The retractor tool 5 comprises a moving member, a cradle 8, arranged to slide along the rails 7. The measuring device 4 is put in the cradle 8. As the measuring device 4 slides between the rails 7 the rails 7 provide axial guidance resulting in a good alignment of the measuring device 4.

The retractor tool 5 comprises an open structure. The open structure of the retractor tool 5 provides an improved visibility to the measuring device 4. The retractor tool 5 can comprise a light stainless structure.

The retractor tool 5 comprises a driving mechanism 9 for moving the cradle 8. An example of the driving mechanism 9 is shown in the Figures. A threaded shaft 16, e.g. a screw bar, is fixed to the cradle 8. A hand-wheel 17 is attached to the rail part. The hand-wheel 17 has a thread nut and the operation of the hand-wheel 17 causes the cradle to move along the rails 7 as the threaded shaft 16 pulls or pushes the end plate of the cradle 18. The hand-wheel 17 can be detachable, for instance, and removed from the arrangement 1 when it is not needed.

The driving mechanism 9 has preferably a self-locking property, which means that the axial loading caused to the cradle 8 by process space 3 pressure will not cause the cradle 8 moving backwards.

Figure 2:
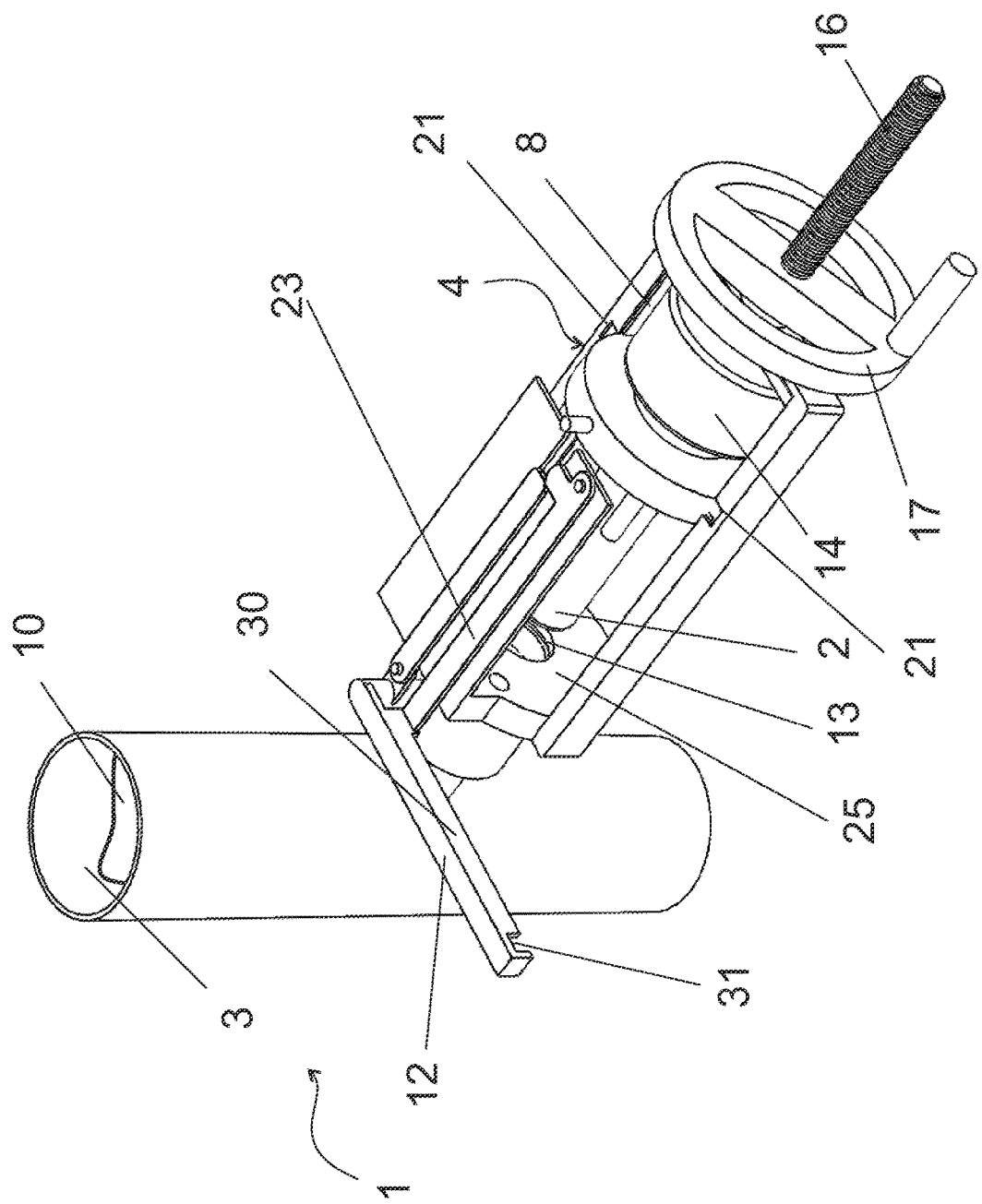
FIG. 2 shows the arrangement in the beginning of the inserting of a head of a measuring device to a process space.

FIG. 2 shows the arrangement 1 in the beginning of the inserting of a head of a measuring device 2 to a process space 3.

The measuring device 4 is put to the cradle 8 the head of the measuring device 2 facing the process space 3. The measuring device 4 preferably comprises projecting parts 19, 19a, 19b and the cradle 8 comprises recesses 20, 20a, 20b providing a form locking, i.e. a form locking connection, which is made by at least partially enveloping of the outer contour of the projecting part 19, 19a, 19b with the recess 20, 20a, 20b. The projecting parts 19, 19a, 19b can comprise different sizes as well as the corresponding recesses 20, 20a, 20b. Then the measuring device 4 is installable to the cradle 8 only into one position, e.g. the valve lock operator 24 upwards. The end plate 18 of the cradle 8 prevents tilting of the measurement device 4 when the measuring device 4 rests in the cradle 8. The end plate 18 of the cradle 8 provides also support to the measuring device 4 against compressive axial loading F caused by pressure of the process space 3. It is also possible to use other attachment means for keeping the measuring device 4 inside the cradle 8 in addition or instead of the presented form locking connection. Examples of other attachment means are locking nuts.

Figure 15:
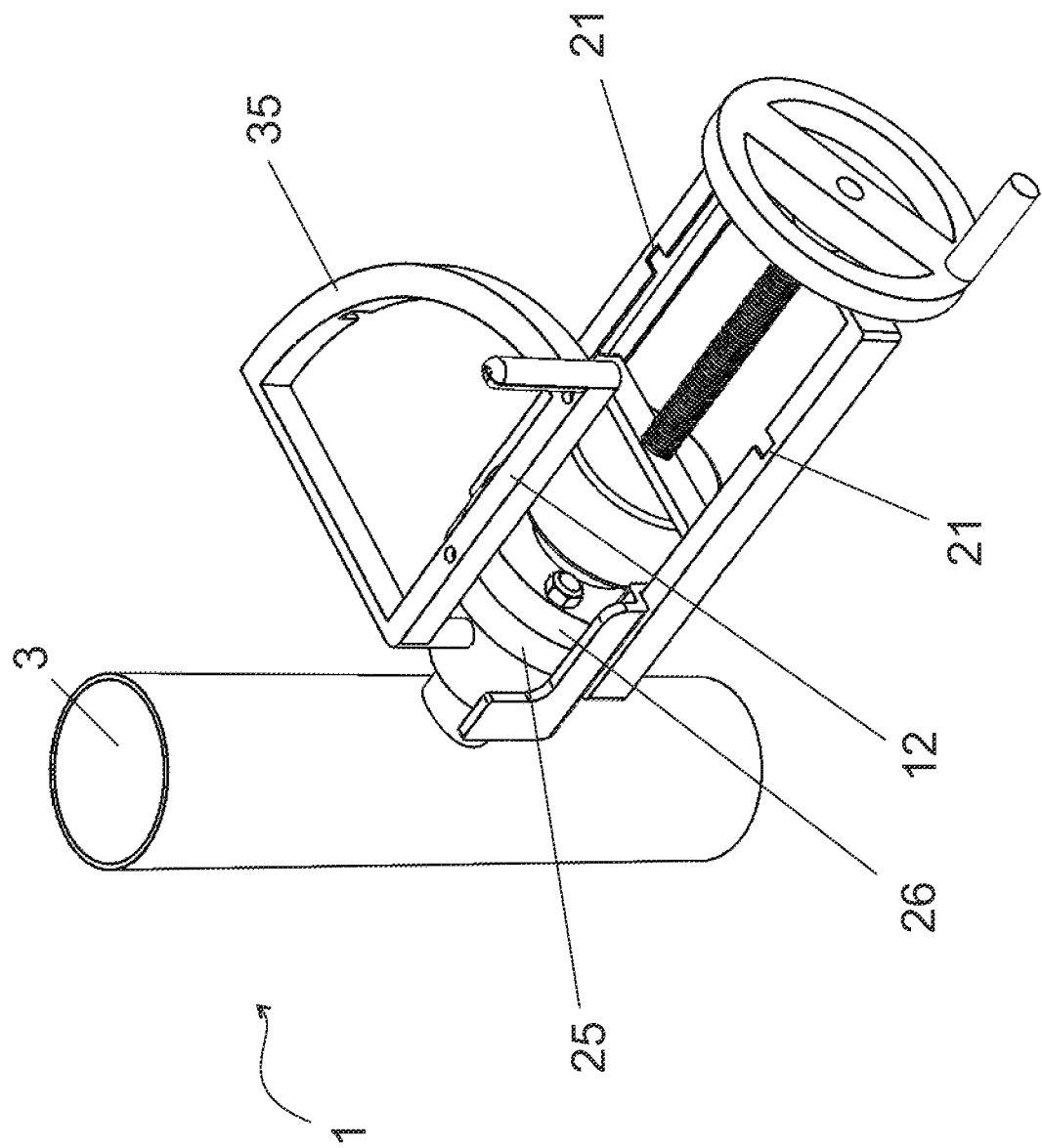
FIG. 15 shows the arrangement when the head of a measuring device is inserted to the process space.

The rails 7 comprise openings 21 at the corresponding locations where the recesses 20 of the cradle 8 are located when the cradle 8 is in a position where the loading of the measurement device 4 to the cradle 8 can be done. These locations are shown in FIGS. 1, 2 and 15.

The rails 7 shown in Figures are having a form of C-channel where two sides are bend to form a C. The cradle 8 shown in Figures comprises two sides 22 connected with an end plate 18. The sides 22 of the cradle 8 are sliding within the rails 7 where the lower part of the rail 7 prevents the cradle 8 from falling down and the upper part of the rail 7 prevents the cradle 8 from being pulled upwards.

In the beginning of the inserting of a head of a measuring device 2 to a process space 3 the isolation valve 11 is in a closed position. The valve lock mechanism prevents the opening of the isolation valve 11. The valve lock mechanism comprises a valve lock part 23 and a valve lock operator 24. The valve lock part 23 is arranged to the valve member 6 and it mechanically prevents rotation of the valve handle 12. The valve handle 12 acts as a part of a safety locking system of the arrangement 1 as the valve member 6 should not be opened if the measuring device 4 is not at a location where it bars the fluid 10 flow from the process space 3. The valve lock operator 24 is arranged to the measuring device 4. The valve lock part 23 extends above the rails 7.

The valve lock mechanism is released by moving the cradle 8 containing the measuring device 4 towards the process space 3 and pushing the valve lock part 23 with the valve lock operator 24 causing a rotation of the valve lock part 23 which unlocks a rotation of the valve handle 12.

In the Figures the valve lock part 23 is a pivoting elongated part connected to an isolation valve flange 25. The valve lock operator 24 comprises a protruding part, a pin. The protruding part is formed to the body of the measuring device 14 extending outside the valve member 6 when the head of the measuring device 2 is in the inserted position in the process space 3. In Figures the protruding part is formed to an outer surface of a flange of the measuring device 26. The valve lock mechanism provides a synchronized operation between the rotation of the valve handle 12 and the axial movement of the measuring device 4.

Figure 3:
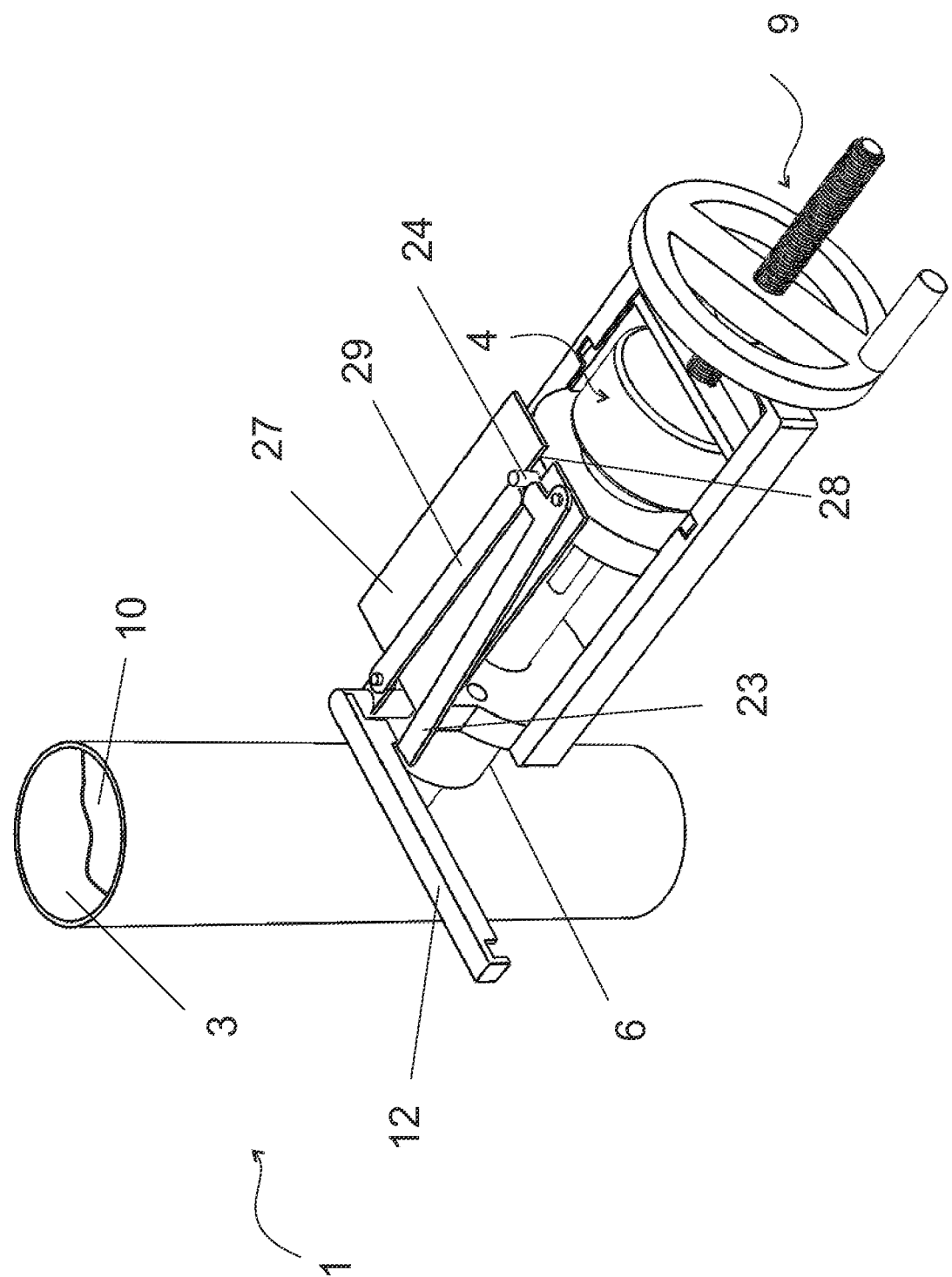
FIG. 3 shows the arrangement in the phase of the inserting of the head of a measuring device to the process space.

FIG. 3 shows the arrangement in the phase of the inserting of a head of a measuring device 2 to a process space 3. The driving mechanism 9 has moved the cradle 8 containing the measuring device 4 towards the process space 3. The head of the measuring device 2 has arrived in the sealing gasket part 13 of the valve member 6. The sealing gasket part 13 provides sealing between the measuring device 4 and the isolation valve body.

The isolation valve 11 is still in a closed position. As the measuring device 4 has entered the sealing gasket part 13 of the valve member 6 it is safe to start opening the isolation valve 11 and the valve lock mechanism can be released.

The valve lock mechanism is released with the protruding part of the valve lock operator 24. When the protruding part of the valve lock operator 24 reaches the valve lock part 23 and moves forward it pushes the valve lock part 23. The pushing of the valve lock part 23 causes the valve lock part 23 to rotate which rotation moves the end of the valve lock part 23 away from blocking the rotation of the valve handle 12.

The arrangement 1 preferably comprises a guide plate 27 comprising a guide groove 28 extending above the rails 7. The protruding part of the valve lock operator 24 can move in the guide groove 28 which provides sideways support.

The arrangement 1 preferably comprises a collision prevent part 29 preventing the measuring device 4 from colliding with a closed valve member 6 in the insertion phase. The head of the measuring device 2 comprises sensitive parts and there is a risk of damage if a collision occurs. The collision prevent part 29 is attached to the valve handle 12 and when the isolation valve 11 is closed it slides over the guide groove 28.

Figure 4:
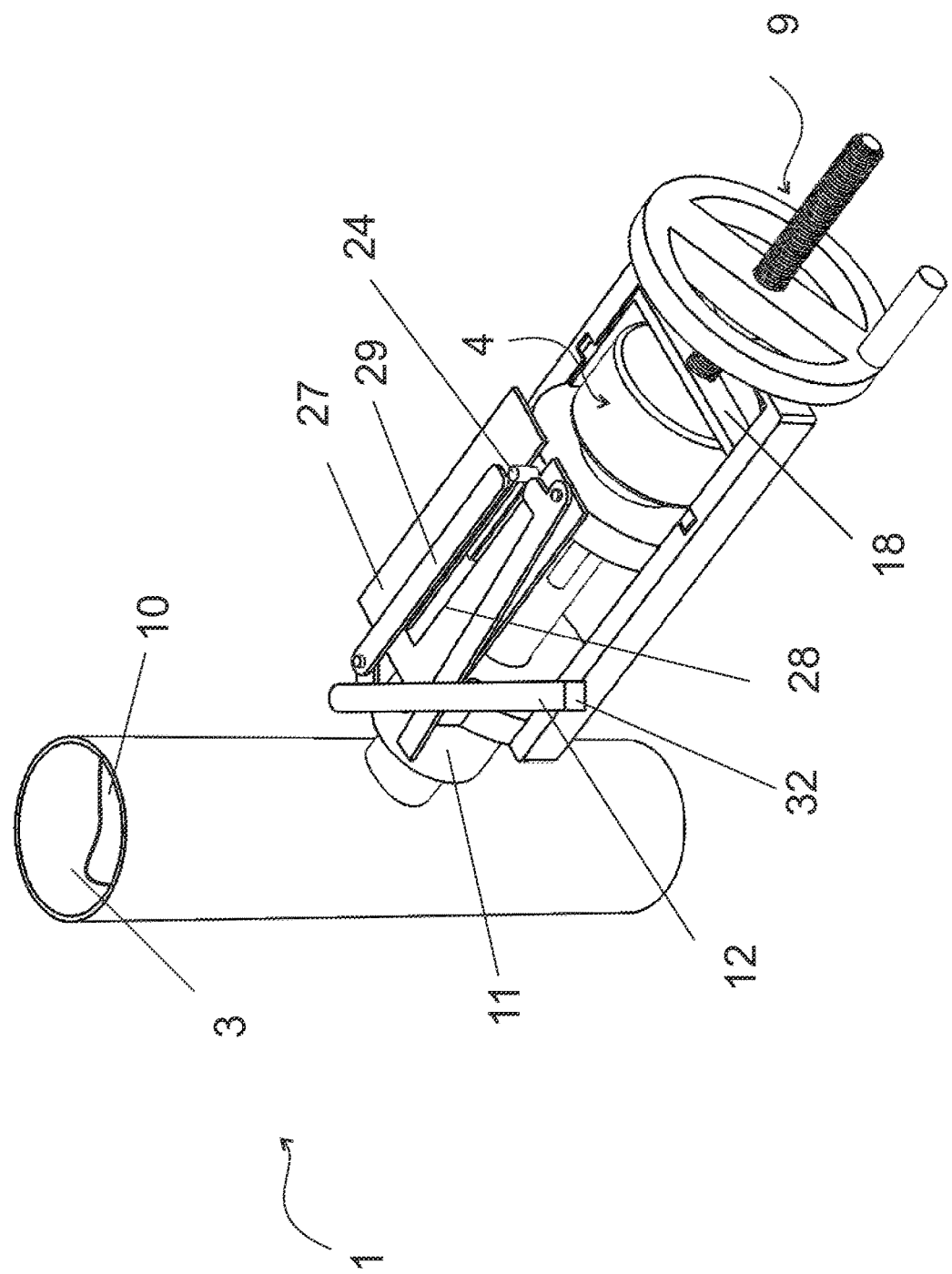
FIG. 4 shows the arrangement in the phase of the opening isolation valve.

FIG. 4 shows the arrangement in the phase of the opening isolation valve. In FIG. 4 the valve handle 12 of the isolation valve 11 is rotated. As the isolation valve 11 is opened the pressure from the process space 3 pushes the measuring device 4 against the cradle 8 and the driving mechanism 9.

The collision prevent part 29 pivoted to the valve handle 12 has moved along the valve handle 12 exposing the guide groove 28. The head of the measuring device 2 moves through the valve member 6 when the isolation valve 11 is open.

Figure 5:
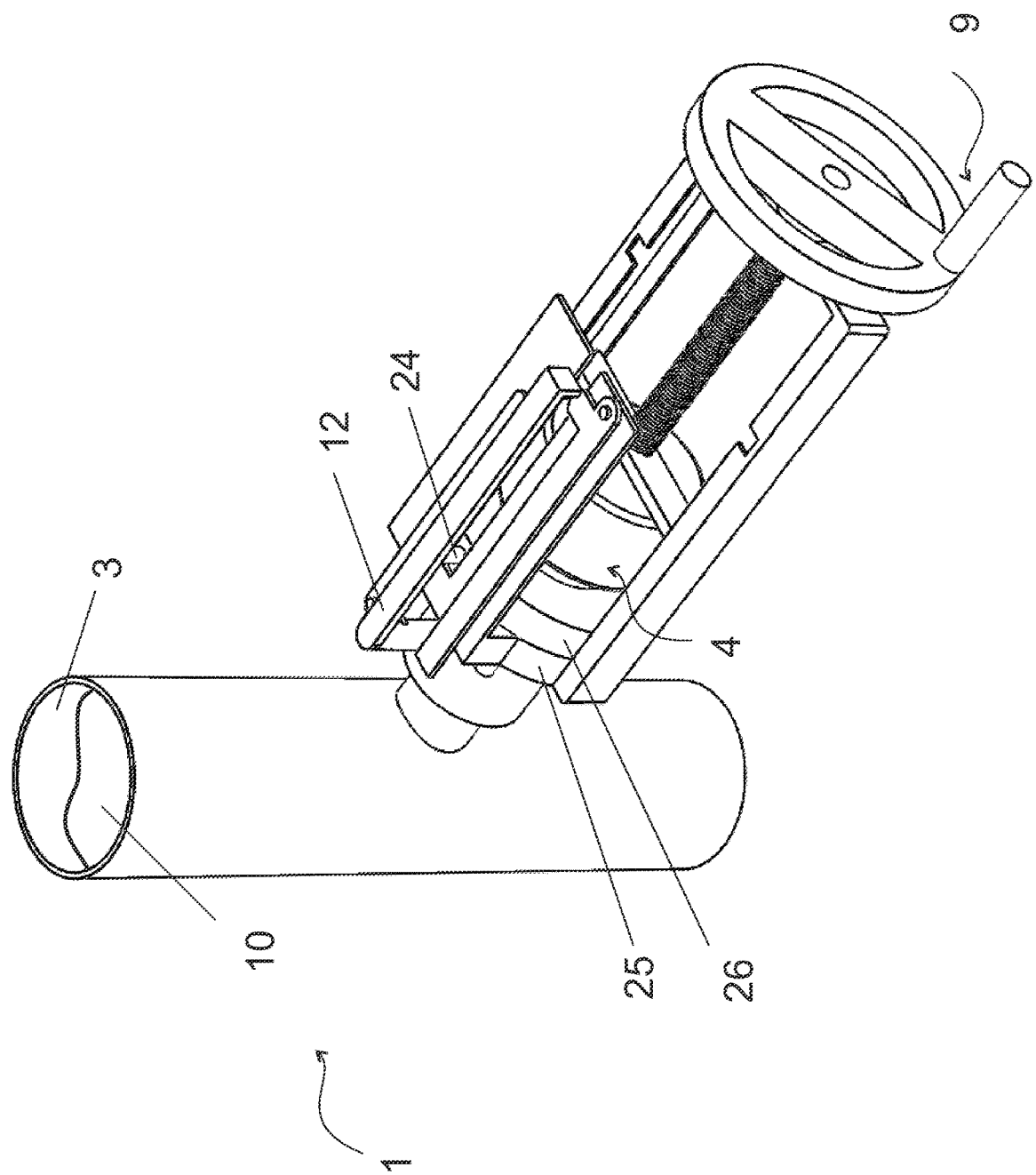
FIG. 5 shows the arrangement when the head of a measuring device is inserted to the process space.

In FIG. 5 the measuring head of the measuring device 2 is inserted in the process space 3. The measuring head 2 extends into the process space 3 and the measuring head 2 is in contact with fluid 10 to be measured contained in the process space 3 or flowing therein.

The flange of the measuring device 26 is attached to the isolation valve flange 25. The joint can comprise a bolt-and-screw joint, for instance.

The joint between the measuring device 4 and the isolation valve 11 receives the pressure from the process space 3.

Figure 6:
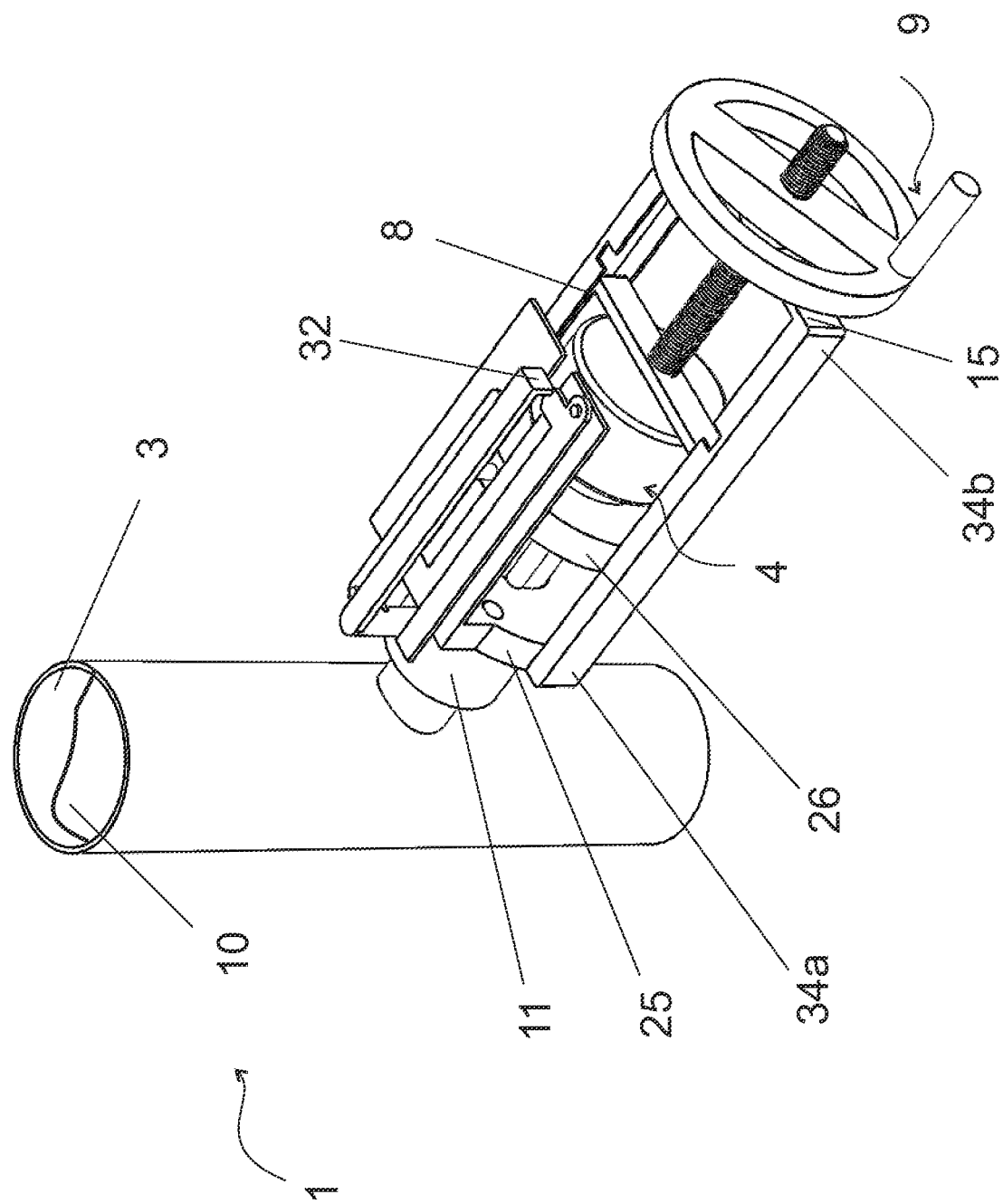
FIG. 6 shows the arrangement in the phase of the removing of the head of the measuring device from the process space.
Figure 7:
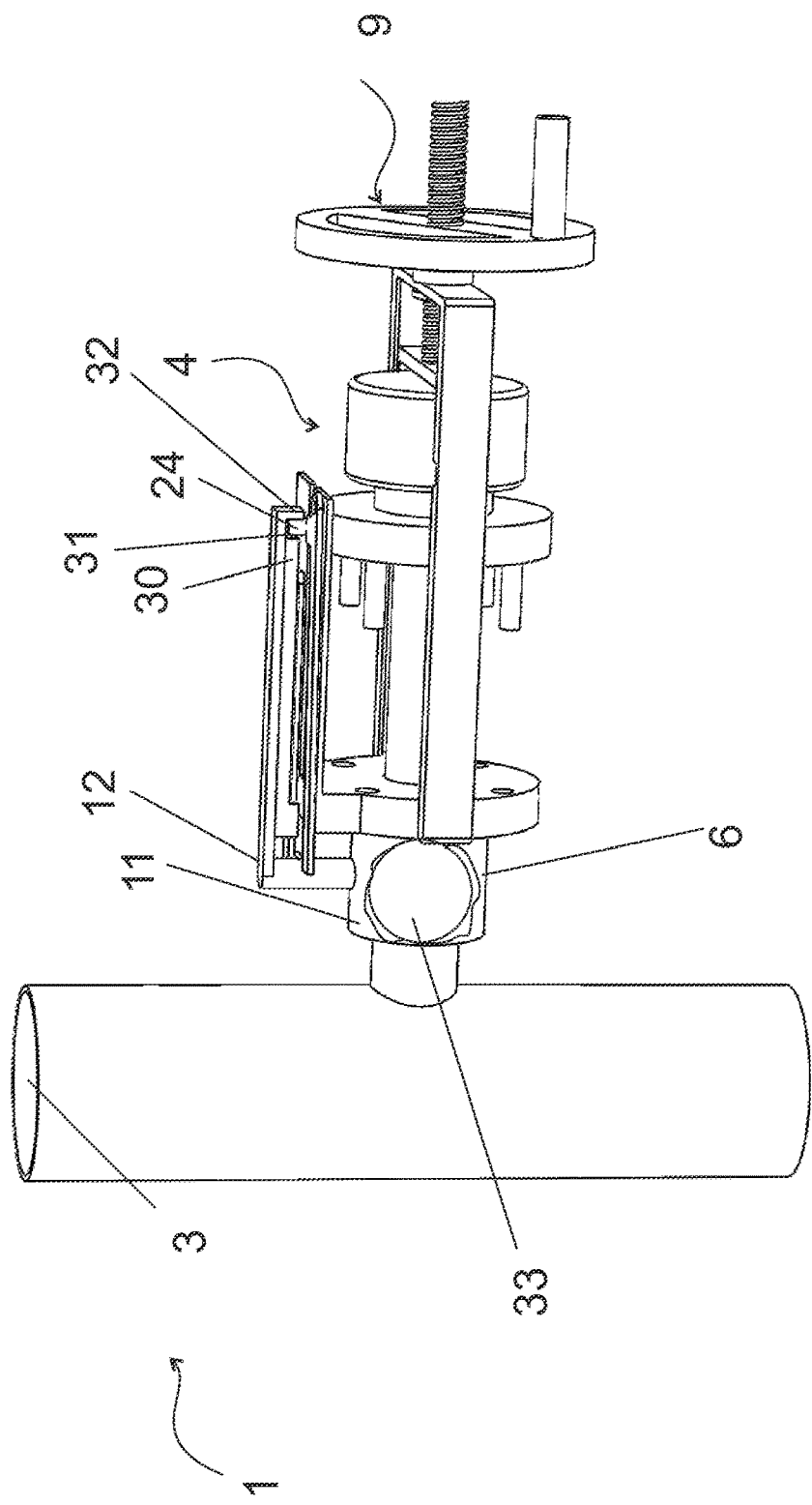
FIG. 7 shows the arrangement in the phase of the removing of the head of the measuring device from the process space.

FIGS. 6 and 7 show the removal of the head of the measurement device 2 from the process space 3. FIGS. 4-1 are also used to describe the removing the head of the measuring device 2 from the process space 3 as even though the operation of the arrangement 1 is the opposite the locations of the arrangement 1 parts are similar in the removal and insertion processes.

In FIG. 6 the isolation valve 11 is fully open. The joint between the measuring device 4 and the isolation valve 11 is unlocked and the pressure from the process space 3 pushes the measuring device 4 against the cradle 8 and the driving mechanism 9. The driving mechanism 9 is moving the cradle 8 away from the process space 3.

The valve handle 12 preferably comprises a stop bar 30 at its axial side. The stop bar 30 comprises a slot 31 at its end for the valve lock operator 24. The valve handle 12 can be rotated when the protruding valve lock operator 24 can pass through the slot 31. At the location where the protruding valve lock operator 24 can pass through the opening the head of the measuring device 2 is in the sealing gasket part 13 of the valve member 6. This location of the protruding valve lock operator 24 is shown in FIG. 7. Otherwise the stop bar 30 blocks the movement of the valve handle 12 when it hits the protruding valve lock operator 24.

The aim of the stop bar 30 is to prevent the closing of the closure element 33 of the valve member 6 by turning the valve handle 12 when the measuring device 4 is at the operation area of the closure element 33. The stop bar 30 protects both the valve closure element 33 and the measuring device 4 as both of them could be damaged if the closure element 33 is trying to close while the measuring device 4 is in the closure element 33 opening.

The stop bar 30 extends in axial direction when the valve member 6 is open and it provides also guiding to the measuring device 4 comprising the valve lock operator 24 by supporting the valve lock operator 24 sideways.

In FIG. 7 the isolation valve 11 is still fully open. The valve handle 12 preferably comprises a stopper 32 at its end. The stopper 32 halts the movement of the measuring device 4 and the cradle 8 at a location when the head of the measuring device 2 is outside the isolation valve 11. At the location of the halting, the head of the measuring device 2 is in the sealing gasket part 13 of the valve member 6 where it bars the fluid 10 flow from the process space 3. The stopper 32 prevents the removal of the head of the measuring device 2 from the valve member 6 when the closure element 33 of the valve member 6 is open thereby protecting the user from a fluid spill from the process space 3.

In FIG. 7 the valve handle 12 is parallel to the guide groove 28 and above the guide groove 28. The end of the valve handle 12 comprises a wall part, the stopper 32, extending downwards towards the measuring device 4. As the protruding part of the valve lock operator 24 moves in the guide groove 28 it is halted by the wall part.

The valve handle 12 is then rotated to close the isolation valve 11. This phase is shown in FIG. 4 where the rotation of the valve handle 12 is now made to opposite direction than in the case of insertion. By the rotation of the valve handle 12 the stopper 32 is moved out of a way to permit the valve lock operator 24 continue moving away from the process space 3 in the guide groove 28.

When the isolation valve 11 is closed the pressure from the process space 3 pushes against the closure element 33 of the valve member 6. The closure element 33 of the valve member 6 is shown in FIG. 7 by cutting a part of the body of the valve member 6 surrounding the closure element 33 away. The shown isolation valve 11 is a ball valve where the closure element 33 comprises a ball.

When the valve handle 12 is rotated to close the valve member 6 the collision prevent part 29 pivoted to the valve handle 12 is sliding over the guide groove as shown in FIG. 3. Also the protruding part of the valve lock operator 24 is reaching the valve lock part 23 and it pushes the valve lock part 23 causing a rotation of the valve lock part 23 which locks the rotation of the valve handle 12 as shown in FIG. 2. The valve lock part 23 can be spring-loaded to ensure its operation.

In FIG. 2 the driving mechanism 9 has moved the cradle 8 containing the measuring device 4 to a location where the form locking connection is open and the measuring device 4 can be pulled out from the cradle 8.

The valve lock operator 24 acts in several safety creating functions in the arrangement 1. The valve lock operator 24 operates the valve lock mechanism, and co-operates with the stop bar 30 and the stopper 32. In Figures the valve lock operator 24 is shown as a one part. However, the valve lock operator 24 can comprise two parts, for instance, arranged axially one after each other. The axial length of the valve lock operator 24 depends on the axial length of the sealing gasket part 13 as it is relevant that the head of the measuring device 2 is within the sealing gasket part 13 when opening and closing the valve member 6.

FIGS. 8-15 show another embodiment of the arrangement. In FIGS. 8-15, the same reference numerals as in FIGS. 1-7 are used at corresponding points.

Figure 8:
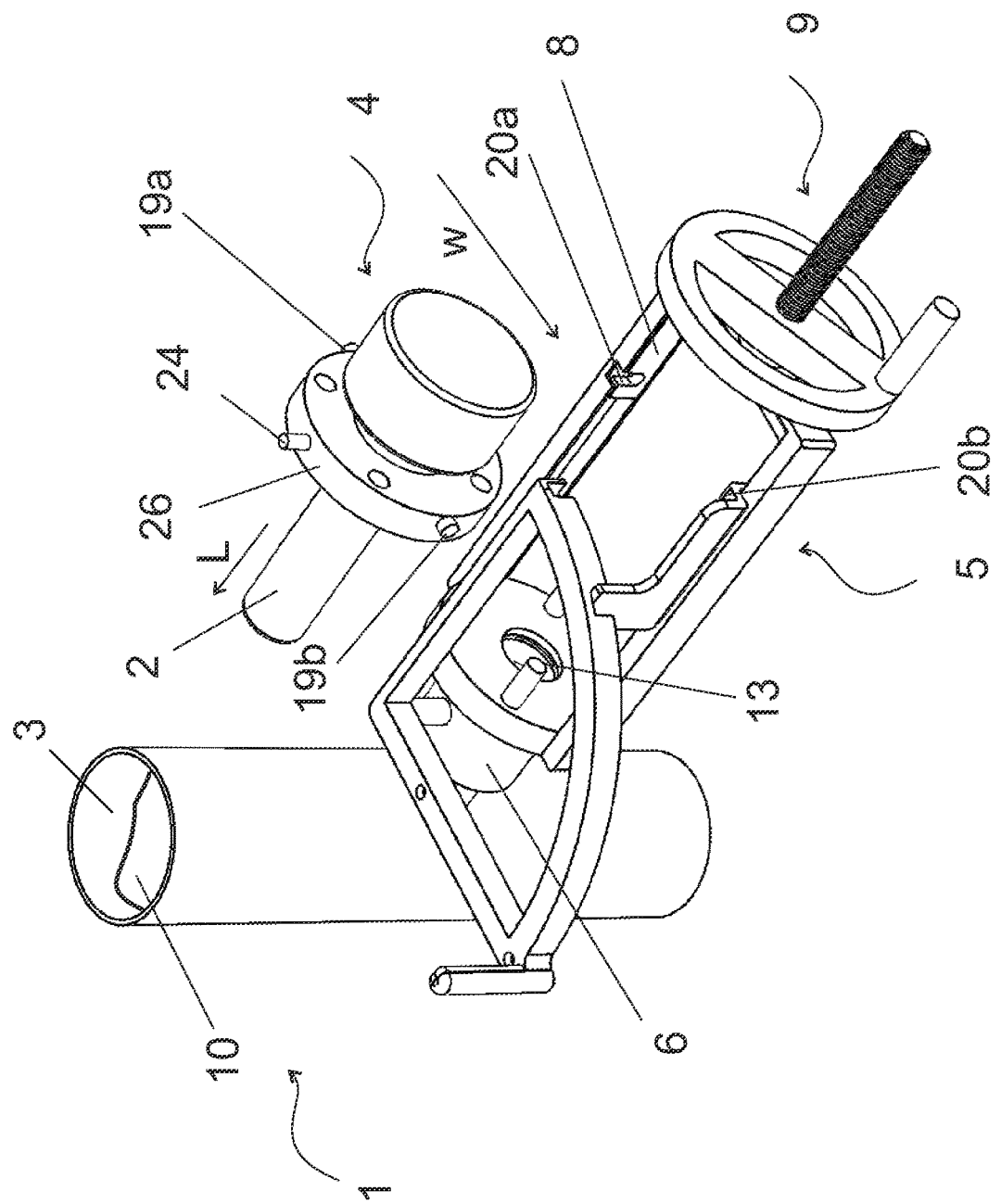
FIG. 8 shows an arrangement where a measuring device is uninstalled to a retractor tool.

FIG. 8 shows the arrangement where a measuring device 4 is uninstalled to a retractor tool 5. FIG. 8 shows an arrangement 1 for inserting and removing a head of a measuring device 2 to and from a process space 3. The arrangement 1 comprises a process space 3, a measuring device 4 comprising a measuring head 2 at its one end and a retractor tool 5. A valve member 6 is connected to the process space 3 and the retractor tool 5 is connected to the valve member 6.

The retractor tool 5 comprises rails 7 and a cradle 8 for receiving the measuring device 4 and arranged to slide along the rails 7. The cradle 8 is ready to receive or deliver the measuring device 4 when the cradle 8 is at its outermost position and the openings 21 of the rails and the recesses 20a,b of the cradle 8 overlap.

The flange of the measuring device 26 is attached to the isolation valve flange 25. In the FIGS. 8-15 the bolts are fixed to the isolation flange 25 and the flange of the measuring device 26 comprises bolt holes. The valve lock operator 24 arranged to the measuring device 4 corresponds the valve lock operator described in previous embodiment.

Figure 12:
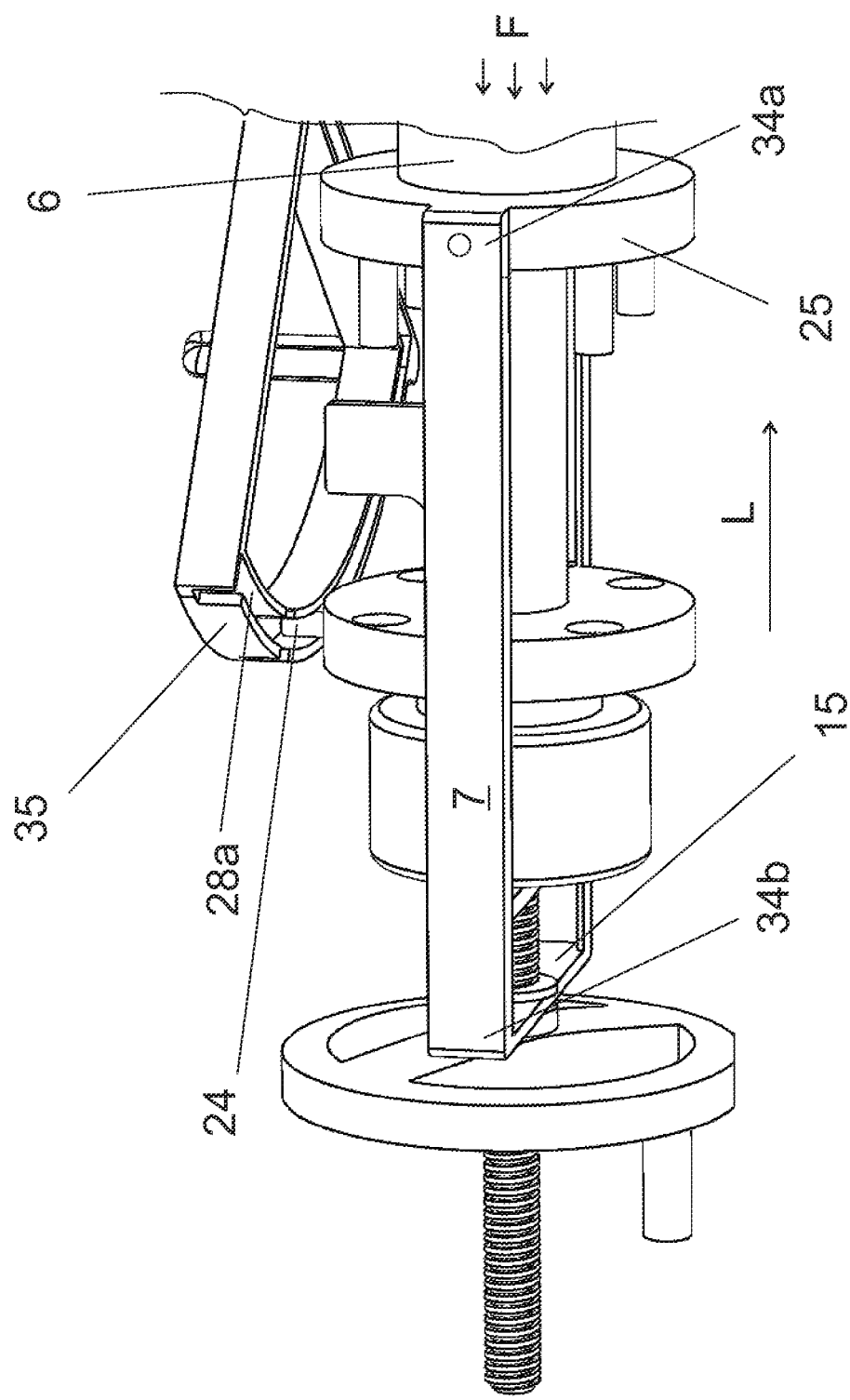
FIG. 12 shows the arrangement in the phase of the opening isolation valve.

FIG. 12 shows the structure of the rail part of the retractor tool 5. The first ends 34a of the rails 7 are attached to the valve member 6. The rails 7 are attached to an isolation valve flange 25 of the valve member 6. The second ends of the rails 34b are connected with a cross beam 15. The rail part forms a protective frame, which encircles the cradle 8 and the measuring device 4 in the length direction L and in the width direction w of the measuring device 4 when the measuring device 4 is received in the cradle 8. The cradle 8 is arranged inside the rails 7 and surrounded by the rails 7 allowing the cradle 8 to be removed only by disassembling the rectaractor tool 5. In a fault situation the pressure of the process space 3 can not eject the cradle 8 and the measuring device 4 out of the rail part as the rails 7 arranged on both sides of the measuring device 4 provide sideward support and the cross beam 15 provides support against compressive axial loading F.

The first ends 34a of the rails 7 are attached to an isolation valve flange 25 with a form locking connection and with a bolt joint, for instance. In FIG. 12 shown form locking connection is made by providing the isolation valve flange 25 with protrusions arranged at the circumference of the flange 25 and providing the lower parts of the first ends 34a of the rails 7 with openings. The rails 7 are then installed from above. The top of the bolt joint can be additionally covered which impedes the opening of the bolt joint. The use of two separate attachment means increases user safety. The rail part structure, rails 7 and the cradle 8 correspond the rail part structure, rails 7 and the cradle 8 described in previous embodiment.

The retractor tool 5 comprises a driving mechanism 9 for moving the cradle 8. The driving mechanism corresponds the driving mechanism described in previous embodiment.

The valve member 6 comprises an isolation valve 11, a valve handle 12 for operating the isolation valve 11 and a sealing gasket part 13. In the embodiment shown in FIGS. 8-15 some of the safety features co-operating with the valve handle 12 are arranged in another way. In FIGS. 8-15, a curved guide bar 35 is connected to the valve handle 12. The guide bar 35 comprises a guide groove 28a on its lower surface where the protruding valve lock operator 24 is able to move. The first end of the curved guide bar 36a is connected to the stop bar 30 of the valve handle 12 towards the slot 31 in the stop bar 30 to allow the valve lock operator 24 moving in the guide groove 28a pass through the slot 31. The second end of the curved guide bar 36b is connected to a stiffening beam 37 which extends between the curved guide bar 34 and the valve handle 12.

Figure 9:
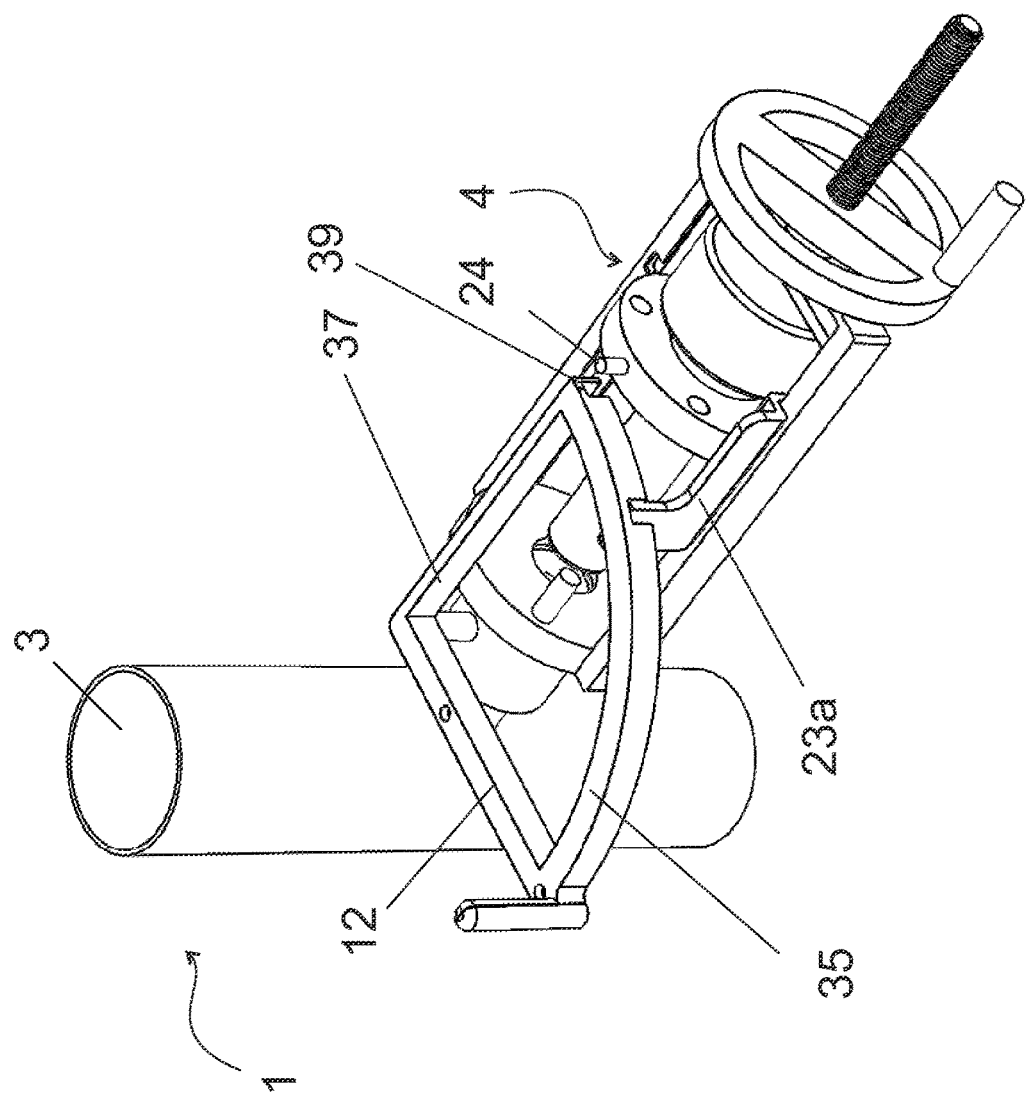
FIG. 9 shows the arrangement in the beginning of the inserting of a head of a measuring device to a process space.
Figure 10:
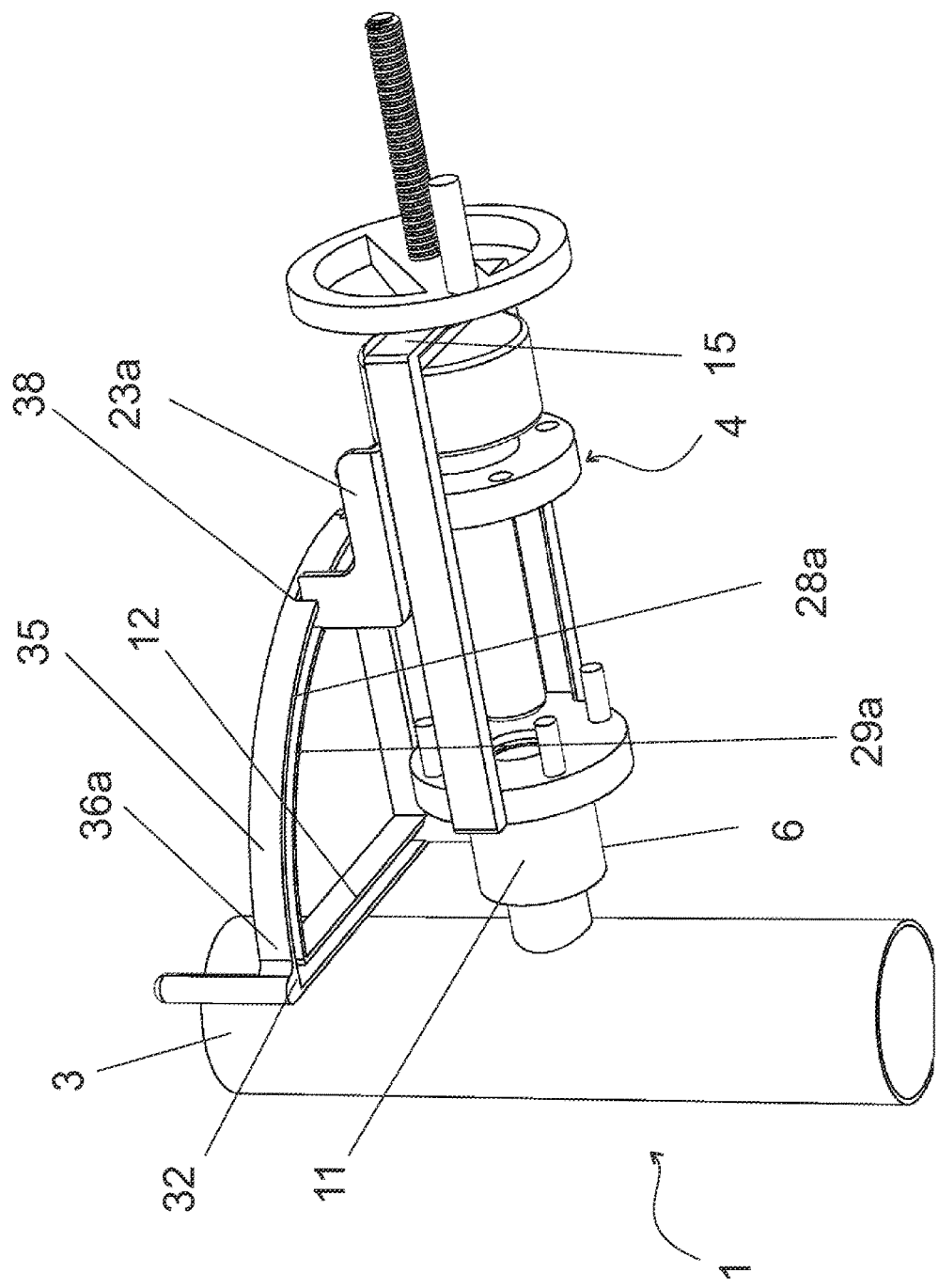
FIG. 10 shows an upwards view of the arrangement in the beginning of the inserting of a head of a measuring device to a process space.

FIG. 9 shows the arrangement in the beginning of the inserting of a head of a measuring device to a process space and FIG. 10 shows an upwards view of the arrangement. The isolation valve 11 is in a closed position. The valve lock mechanism prevents the opening of the isolation valve 11 as the measuring device 4 is not at a location barring a fluid 10 flow from the process space 3. The valve lock mechanism comprises a curved guide bar 35, an elongated valve lock part 23a and a valve lock operator 24. The valve lock part 23a is arranged to the cradle 8 to move with the cradle 8 and it mechanically prevents rotation of the valve handle 12 when the cradle 8 is at its outermost position by extending through a notch 38 formed to the curved guide bar 35. The measuring device 4 is received in the cradle 8. The measuring device 4 is positioned between the inner surfaces of the two rails 7 such that it is able to slide between the rails 7.

Figure 11:
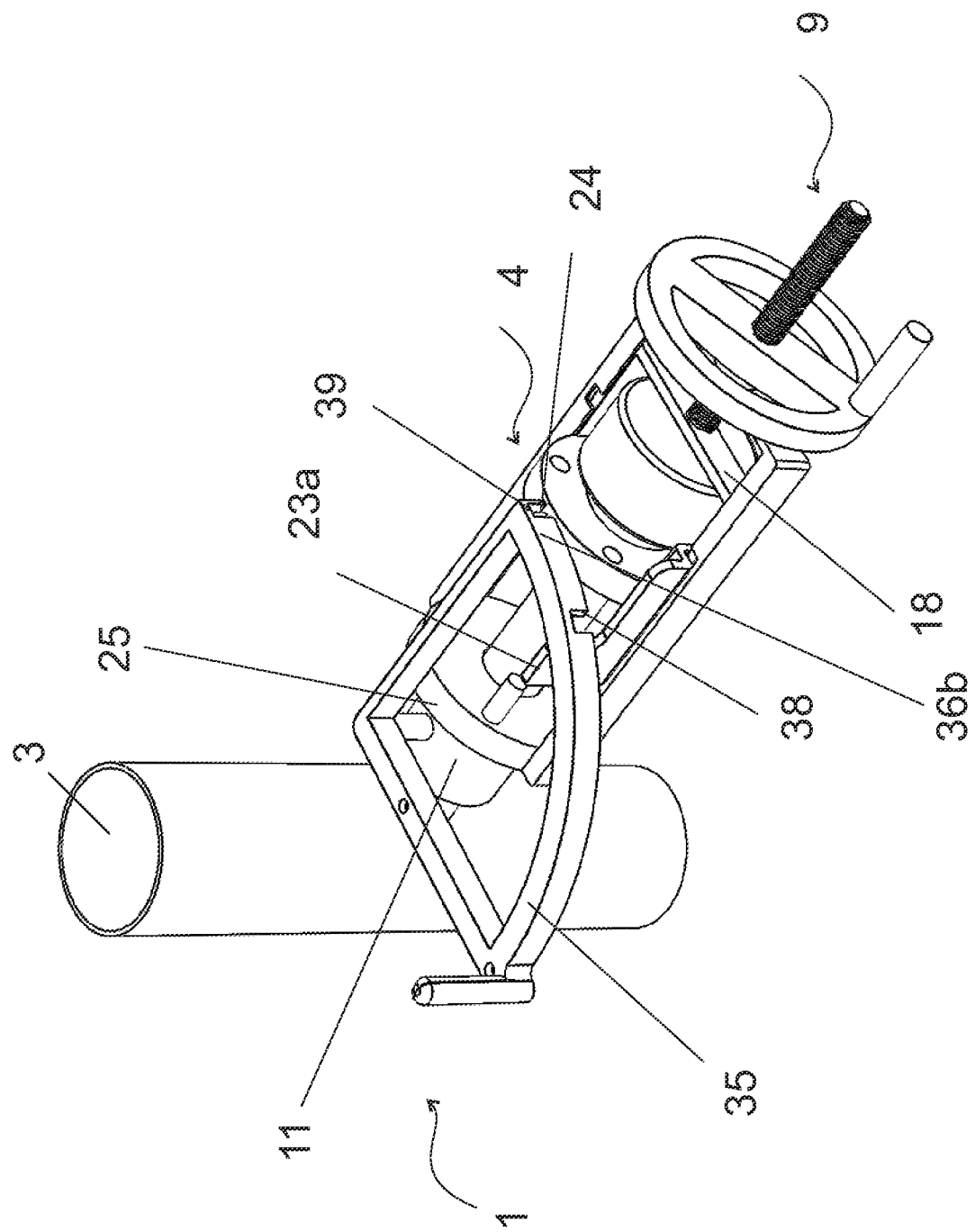
FIG. 11 shows the arrangement in the phase of the beginning of opening of the isolation valve.

FIG. 11 shows the arrangement in the phase of the beginning of opening of the isolation valve. The driving mechanism 9 has moved the cradle 8 containing the measuring device 4 along the rails 7 towards the process space 3. The isolation valve 11 is still in a closed position. The head of the measuring device 2 has arrived in the sealing gasket part 13 of the valve member 6, i.e. the measuring device 4 is at a location barring a fluid 10 flow from the process space 3. As the fluid 10 flow from the process space 3 is blocked with the measuring device 4 it is safe to start opening the isolation valve 11.

The valve lock mechanism is released by moving the cradle 8 containing the measuring device 4 towards the process space 3 causing the valve lock part 23a to advance through a notch 38 in the curved guide bar 35. The valve lock part 23a, its uppermost part, is dimensioned to extend through the notch 38 when the cradle 8 is in its outermost position and between the outermost position and a position where the valve lock operator 24 arranged to the measuring device 4 received in the cradle 8 has not reached the inlet 39 leading into guide groove 28a.

As shown in FIG. 11, the valve lock operator 24 has moved through the inlet 39 and is in the guide groove 28a and the valve lock part 23a has passed through the notch 38. The valve lock mechanism is released, i.e. the rotation of valve handle 12 is unlocked.

The curved guide bar 35 attached to the valve handle 12 forms a collision prevent part 29a preventing the measuring device 4 from colliding with a closed valve member 6 in the insertion phase. The vertical surface of the guide bar 35 facing the valve member 6 forms the collision prevent part 29a by blocking the axial movement of the valve lock operator 24 towards the process space 3 if the valve member 6 is not open.

FIG. 12 shows the arrangement in the phase of the opening isolation valve. In FIG. 12 the valve handle 12 of the isolation valve 11 is rotated and the first end of the curved guide bar 36a moves towards the valve lock operator 24 the valve lock operator 24 being in the guide groove 28a. At this phase the axial movement of the cradle 8 is negligible.

Figure 13:
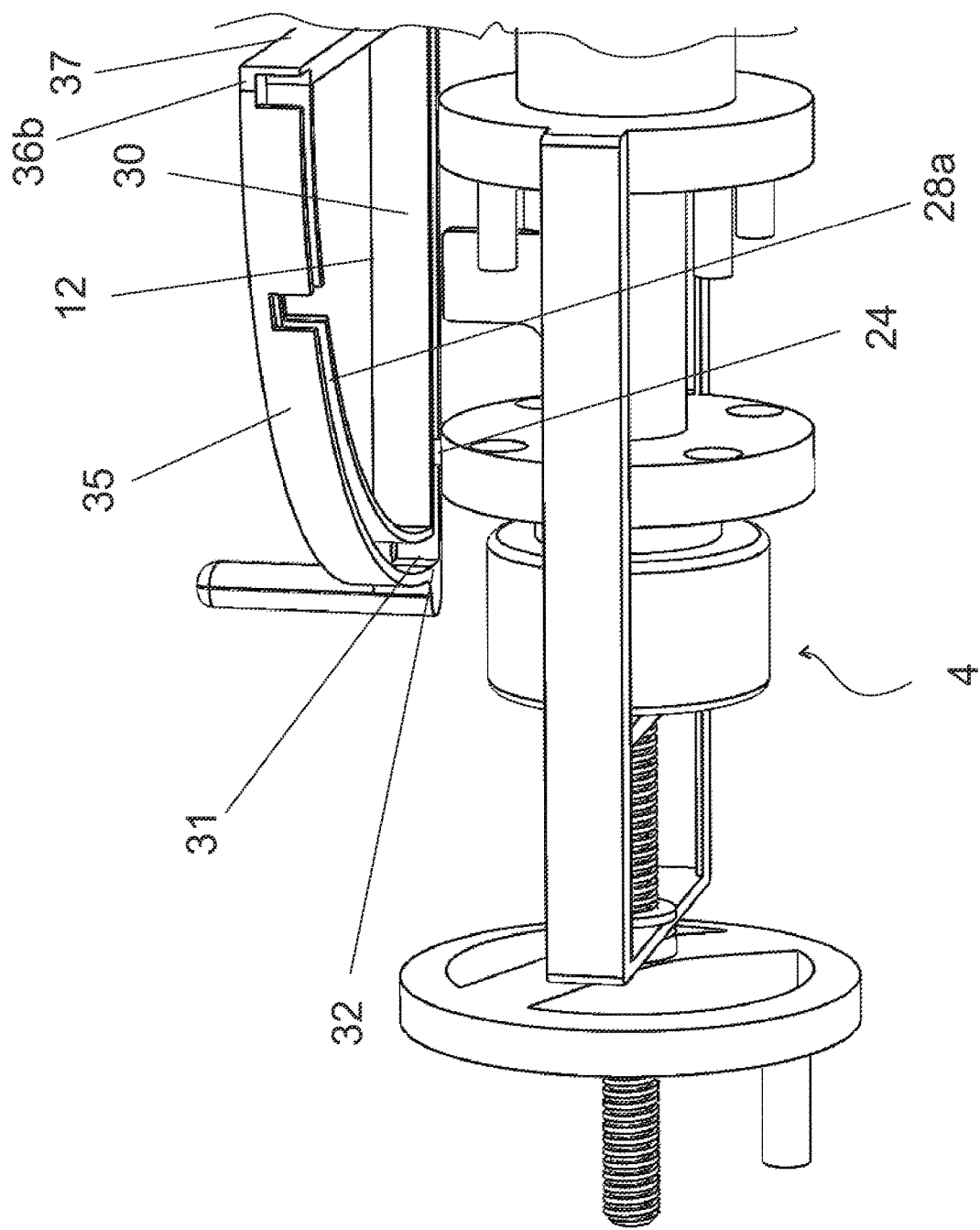
FIG. 13 shows the arrangement in the phase where the isolation valve is open.
Figure 14:
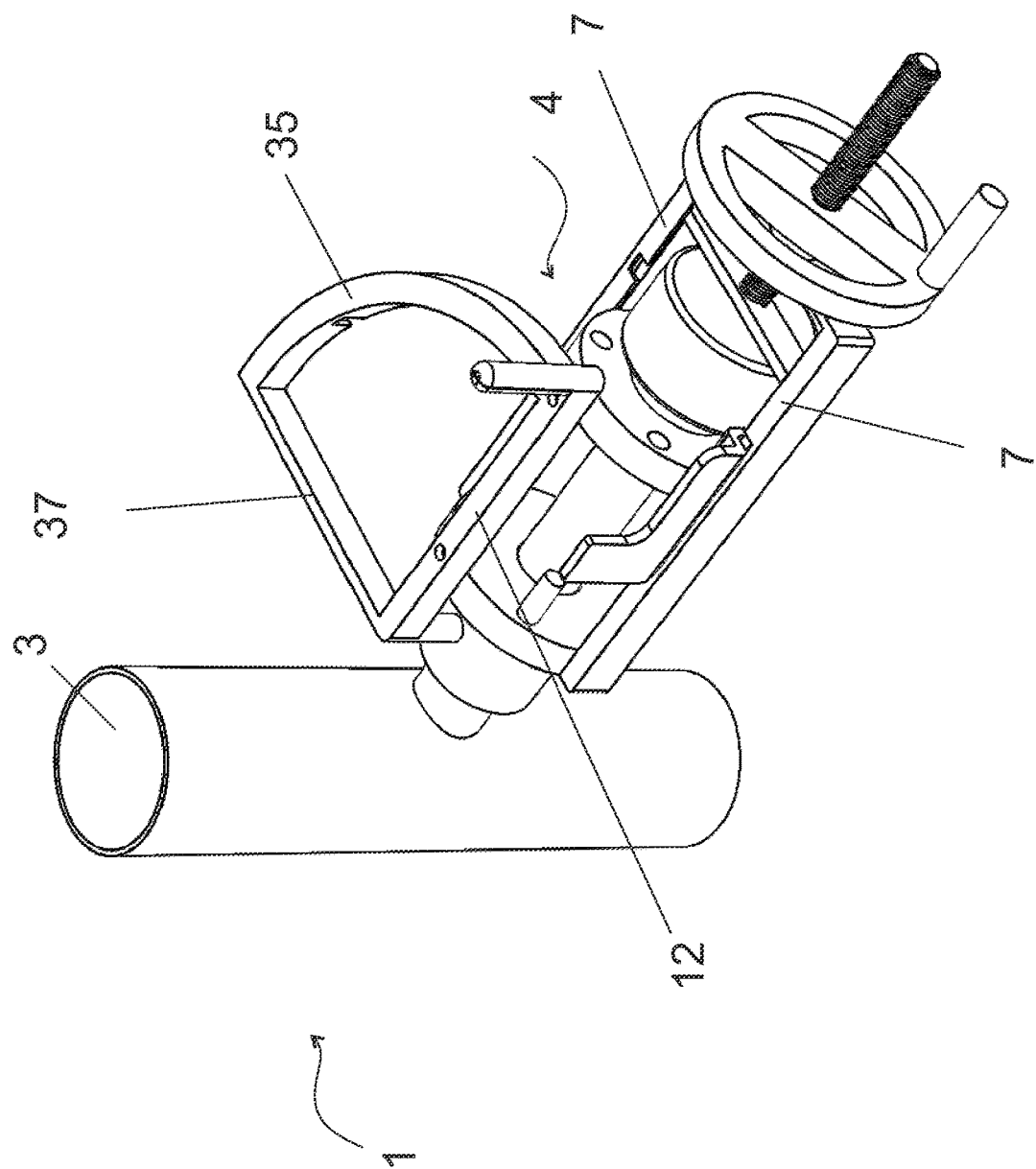
FIG. 14 shows a downwards view of the arrangement in the phase where the isolation valve is open.

FIG. 13 shows the arrangement in the phase where the isolation valve is fully open and FIG. 14 shows a downwards view of the arrangement. By turning the valve handle 12 the protruding valve lock operator 24 has moved in the guide groove 28a to the first end of the curved guide bar 36a and passed through the slot 31 in the stop bar 30. The cradle 8 has moved forward towards the process space 3 by operating the driving mechanism 9. The stop bar 30 extending in axial direction supports the valve lock operator 24 sideways.

FIG. 15 shows the arrangement when the head of a measuring device 2 is inserted to the process space 3. The flange of the measuring device 26 and the isolation valve flange 25 are attached to each other.

FIGS. 15-8 are also used to describe the removing the head of the measuring device 2 from the process space 3 as even though the operation of the arrangement shown in Figures is the opposite the locations of the arrangement 1 parts are similar in the removal and insertion processes.

In FIGS. 14 and 13 the isolation valve 11 is fully open. The joint between the measuring device 4 and the isolation valve 11 is unlocked and the pressure from the process space 3 pushes the measuring device 4 against the cradle 8 and the driving mechanism 9. The driving mechanism 9 is moving the cradle 8 away from the process space 3.

The arrangements comprises a closing mechanism allowing closing of the valve member 6 when the measuring device 4 is at a location barring a fluid 10 flow from the process space 3 and outside an isolation valve 11 of valve member 6. The protective closing mechanism prevents the closing of the valve member 6 while the measuring device 4 is inserted to the valve member 6 and prevents the removal of the measuring device 4 from the fluid 10 flow blocking position while the valve member 6 is open. The closing mechanism comprises the stop bar 30 and the stopper 32 arranged to the valve handle 12. The stop bar 30 and the stopper 32 correspond the stop bar and the stopper described in previous embodiment.

The valve handle 12 can be rotated when the cradle 8 has moved back to a position where the protruding valve lock operator 24 can pass through the slot 31. Otherwise the stop bar 30 blocks the movement of the valve handle 12 when it hits the protruding valve lock operator 24.

The stopper 32 halts the axial movement of the measuring device 4 and the cradle 8 at a location where the head of the measuring device 2 is in the sealing gasket part 13 of the valve member 6.

As shown in FIG. 12 the valve handle 12 is then rotated to close the isolation valve 11. The rotation of the valve handle 12 is now made to opposite direction than in the case of insertion. By turning the valve handle 12 the valve lock operator 24 passes through the slot 31 into the guide groove 28a at the first end of the curved guide bar 36a.

FIG. 11 shows the phase where the valve handle 12 has been rotated such that the valve lock operator 24 has reached the second end of the guide bar 36b. The valve lock operator 24 is ready to exit the guide bar 35 through the inlet 39 by operating of the driving mechanism 9 pulling the cradle 8.

In FIGS. 10 and 9 the driving mechanism 9 has moved the cradle 8 containing the measuring device 4 to its outermost position and the measuring device 4 can be pulled out from the cradle 8. The valve lock part 23a extends through the notch 38 formed to the curved guide bar 35 and blocks the rotational movement of the valve handle 12.

In FIGS. 8-15 shown the valve handle 12, the curved guide bar 35 and the stiffening beam 37 which are connected to each other form a shape of a sector of a circle.

The cradle 8 can comprise a curved support beam between the two sides of the cradle 22 for supporting the measuring device 4 from below. Further, the measuring device 4 can comprise a ribbing of the cover at the other end opposing the measuring head 2. The ribbing may serve the purpose of increased outer surface of the measuring device 4 for increased heat transfer. Then the curved support beam positioned between two adjacent ribs supports the measuring device 4 from below and also in axial direction.

In the arrangement the valve member 6, the measuring device 4 and the traction tool 5 are positioned in one side of the process space 3. In the arrangement 1 shown in Figures in the process space 3 comprises one opening for the connection between the fluid 10 in the process space 3 and the head of measuring device 2. The operation from one side of the process space 3 saves also space needed for operating the arrangement.

An apparatus comprises a valve member 6 connectable to a process space 3, a measuring device 4 comprising a measuring head 2 at its one end; a retractor tool 5 connected to the valve member 6, wherein the retractor tool 5 comprises rails 7, the first ends of the rails 34a are attached to the valve member 6 and the second ends of the rails 34b are connected with a cross beam 15, a cradle 8 configured to receive the measuring device 4 and arranged to slide along the rails 7, the measuring device 4 is arranged to slide between the rails 7 when received in the cradle 8, and a driving mechanism 9 configured to move the cradle 8; the driving mechanism 9 is configured to move the measuring head of the measuring device 2 through the valve member 6 into the process space 3 and out of the process space 3; the retractor tool 5 comprises a valve lock mechanism configured to prevent opening of the valve member 6 when the measuring head 2 is not located in the valve member 6.

The arrangement and the apparatus are advantageous for measuring devices used in in-line measurements. The arrangement and the apparatus provide a fool proof and a failsafe construction.

It will be obvious to a person skilled in the art that, as the technology advances, the inventive concept can be implemented in various ways. The invention and its embodiments are not limited to the examples described above but may vary within the scope of the claims.

List of parts: 1 an arrangement; 2 a head of a measuring device, 3 a process space; 4 a measuring device; 5 a retractor tool; 6 a valve member; 7 rails; 8 a cradle; 9 a driving mechanism; 10 fluid; 11 an isolation valve; 12 a valve handle; 13 a sealing gasket part; 14 a body of measuring device; 15 a cross beam;

16 a threaded shaft; 17 a hand-wheel; 18 an end plate; 19, 19a, 19b a projecting part; 20, 20a, 20b a recess; 21 an opening; 22 a side of a cradle; 23, 23a a valve lock part; 24 valve lock operator; 25 an isolation valve flange; 26 a flange of the measuring device; 27 a guide plate; 28, 28a a guide groove; 29, 29a a collision prevent part; 30 a stop bar; 31 a slot; 32 a stopper; 33 a closure element; 34a,b an end of a rail; 35 a guide bar; 36a,b an end of a guide bar; 37 a stiffening beam; 38 a notch; 39 an inlet; F an axial loading; L a length direction; w a width direction.

The invention claimed is:

1. An arrangement for inserting and removing a head of a measuring device to and from a process space, the arrangement comprising[H]:
a measuring device having a measuring head at one end and a retractor tool;
a valve member configured to be connected to a process space, the retractor tool being connected to the valve member, wherein the retractor tool includes: rails, first ends of the rails being attached to the valve member and second ends of the rails being connected with a cross beam, a cradle configured to receive the measuring device and arranged to slide along the rails, the measuring device being arranged to slide between the rails when received in the cradle, and a driving mechanism configured to move the cradle;
a valve lock mechanism configured to prevent opening of the valve member when the measuring device is not at a location barring a fluid flow from a process space, the head of the measuring device being configured to be insertable to a process space and removable from that process space when the measuring device is received in the cradle; and
a collision prevent part configured to prevent the measuring device from colliding with the valve member when closed by blocking an axial movement of the valve lock operator.

2. An arrangement according to claim 1, wherein the valve member comprises:

an isolation valve, a valve handle being configured to operate the isolation valve and a sealing gasket part.

3. An arrangement according to claim 2, wherein the valve lock mechanism comprises:
a curved guide bar connected to the valve handle, a valve lock part and a valve lock operator.

4. An arrangement according to claim 3, wherein the valve lock operator comprises:
a protruding part arranged relative to the measuring device.

5. An arrangement according to claim 4, wherein the curved guide bar comprises:
a guide groove where the protruding part of the valve lock operator is moveable.

6. An arrangement according to claim 5, comprising:
a collision prevent part configured to prevent the measuring device from colliding with the closed valve member when closed by blocking an axial movement of the valve lock operator.

7. An arrangement according to claim 6, comprising:
a closing mechanism configured to close the valve member when the measuring device is at a location barring a fluid flow from a process space and outside an isolation valve of the valve member.

8. An arrangement according to claim 7, wherein the valve handle comprises:
a stop bar at its axial side, the stop bar having a slot at its end for the valve lock operator.

9. An arrangement according to claim 8, in combination with a process space, wherein the valve member, the measuring device and the retractor tool are positioned in one side of the process space.

10. An arrangement according to claim 1, wherein the collision prevent part comprises:
a vertical surface of the curved guide bar facing the valve member.

11. An arrangement according to claim 1, comprising:
a closing mechanism configured to close the valve member when the measuring device is at a location barring a fluid flow from a process space and outside an isolation valve of the valve member.

12. An arrangement according to claim 2, wherein the valve handle comprises:
a stopper, the stopper being capable of halting movement of the measuring device and thereby being configured to prevent a removal of the head of the measuring device from the valve member when a closure element of the valve member is open.

13. An arrangement according to claim 3, wherein the valve handle comprises:
a stop bar at its axial side, the stop bar having a slot at its end for the valve lock operator.

14. An arrangement according to claim 1, wherein the measuring device comprises:
projecting parts, and the cradle includes recesses providing a form locking connection between the measuring device and the cradle.

15. An arrangement according to claim 1, in combination with a process space, wherein the valve member, the measuring device and the retractor tool are positioned in one side of the process space.

16. An arrangement according to claim 1, wherein the measurement device is a sensor, an analyser or an optical analyser.

17. A method for inserting and removing a head of a measuring device to and from a process space, the measuring device having a measuring head at its one end and a retractor tool, a valve member to the process space and connecting the retractor tool, the method comprising:

connecting to the valve member, wherein the retractor tool includes rails, first ends of the rails being attached to the valve member and second ends of the rails being connected with a cross beam, a cradle and a driving mechanism, wherein the cradle is configured to receive the measuring device and slide along the rails;

sliding the measuring device between the rails when received in the cradle via the driving mechanism;

actuating a valve lock mechanism of the valve member for preventing opening of the valve member when the measuring device is not at a location barring a fluid flow from the process space;

inserting and the head of the measuring device to the process space and removing the head from that process space after placing the measuring device in the cradle and operating the driving mechanism and the valve member, wherein the valve lock mechanism includes a valve handle, a curved guide bar connected to the valve handle, a valve lock part arranged to the cradle and a valve lock operator arranged to the measuring device; and releasing the valve lock mechanism by moving the cradle containing the measuring device towards the process space with the driving mechanism until the valve lock part has advanced through a notch formed to the curved guide bar and the valve lock operator is in a guide groove of the curved guide bar which unlocks a rotation of the valve handle.

18. An apparatus comprising:

a valve member connectable to a process space;

a measuring device having a measuring head at one end;

a retractor tool connected to the valve member, wherein the retractor tool includes rails, first ends of the rails being attached to the valve member and second ends of the rails being connected with a cross beam, a cradle configured to receive the measuring device and arranged to slide along the rails, the measuring device being arranged to slide between the rails when received in the cradle, and a driving mechanism configured to move the cradle, the driving mechanism being configured to move the measuring head of the measuring device through the valve member into a process space and out of the process space;

a valve lock mechanism configured to prevent opening of the valve member when the measuring head is not located in the valve member; and a closing mechanism configured to close the valve member when the measuring device is at a location barring a fluid flow from a process space and outside an isolation valve of the valve member.

* * * * *